(12) United States Patent
Mercati et al.

(10) Patent No.: US 10,314,877 B2
(45) Date of Patent: Jun. 11, 2019

(54) METHOD FOR LYMPH DRAINAGE

(71) Applicant: ABOCA S.P.A. SOCIETÀ AGRICOLA, Sansepolcro (IT)

(72) Inventors: Valentino Mercati, Sansepolcro (IT); Anna Maidecchi, Sansepolcro (IT)

(73) Assignee: ABOCA S.P.A. SOCIETA' AGRICOLA, Sansepolcro (IT)

(*) Notice: Subject to any disclaimer, the term of this patent is extended or adjusted under 35 U.S.C. 154(b) by 21 days.

(21) Appl. No.: 15/541,592

(22) PCT Filed: Jan. 4, 2016

(86) PCT No.: PCT/IB2016/050023
§ 371 (c)(1),
(2) Date: Jul. 5, 2017

(87) PCT Pub. No.: WO2016/110794
PCT Pub. Date: Jul. 14, 2016

(65) Prior Publication Data
US 2017/0340692 A1    Nov. 30, 2017

(30) Foreign Application Priority Data

Jan. 7, 2015 (IT) .............................. RM2015A0005

(51) Int. Cl.
| | |
|---|---|
| *A61K 36/896* | (2006.01) |
| *A61K 36/28* | (2006.01) |
| *A61K 36/288* | (2006.01) |
| *A61K 36/53* | (2006.01) |
| *A61K 36/70* | (2006.01) |
| *A61K 9/00* | (2006.01) |
| *A61K 9/14* | (2006.01) |
| *A61K 9/20* | (2006.01) |
| *A61K 9/48* | (2006.01) |
| *A61K 47/46* | (2006.01) |

(52) U.S. Cl.
CPC .......... *A61K 36/896* (2013.01); *A61K 9/0019* (2013.01); *A61K 9/0053* (2013.01); *A61K 9/14* (2013.01); *A61K 9/20* (2013.01); *A61K 9/48* (2013.01); *A61K 36/28* (2013.01); *A61K 36/288* (2013.01); *A61K 36/53* (2013.01); *A61K 36/70* (2013.01); *A61K 47/46* (2013.01)

(58) Field of Classification Search
None
See application file for complete search history.

(56) References Cited

U.S. PATENT DOCUMENTS

| | | | |
|---|---|---|---|
| 6,143,300 A | 11/2000 | Stevenot | |
| 2014/0086981 A1* | 3/2014 | Garcia Anton | .......... C07K 7/06 424/450 |

FOREIGN PATENT DOCUMENTS

| | | |
|---|---|---|
| CN | 101 584 758 A | 11/2009 |
| DE | 36 43 000 A1 | 6/1988 |
| EP | 2 662 086 A1 | 11/2013 |
| FR | 2 336 922 A1 | 7/1977 |
| WO | WO 2016/110794 * | 7/2016 |

OTHER PUBLICATIONS

Nourollahi S et al. Butcher's Broom and Selenium Improve Lipedema. Alternative and Integrative Medicine 2(4)2-7, 2013. (Year: 2013).*
Ogawa Y. Recent Advances in Medical Treatment for Lymphedema. Ann Vasc Dis 5(2)139-144, 2012. (Year: 2012).*
Balansard, J. et al. Hepato-Renal Diuretics I. MD Tropicale 11(4)622-644, 1951. (Year: 1951).*
Ciccone V. et al. Efficacy of AdipoDren in Reducing Interleukin-1 Induced Lymphatic Endothelial Hyperpermeability. J of Vascular Research 53(5-6)255-268, Jan. 2017. (Year: 2017).*
International Search Report for PCT/IB2016/050023, four pages (dated Apr. 2016).
Written Opinion of the ISA for PCT/IB2016/050023, seven pages (dated Apr. 2016).
Written Opinion of the IPEA for PCT/IB2016/050023, five pages (dated Dec. 2016).
Anonymous "Cyclo 3 fort et maladie veineuse" *Concours Medicale*, vol. 113, No. 27, p. 2316 (Jan. 1991).
Christa & Soral-Śmietana "Buckwheat grains and buckwheat products—Nutritional and prophylactic value of their components—A review" *Czech Journal of Food Science*, vol. 26, No. 3, pp. 153-162 (Jan. 2008).
Liu & Chu "Medicine composition treat kidney deficient nephrosis comprise Indian mallow herb false starwort root salvia wild buckwheat" *Database WPI*, Week 201002, AN 2009-S18458, XP-002738860 (Nov. 2009).
Sureshkumar "Phytotherapy of chronic venous insufficiency" *Hygeia—J. Drugs Med.*, vol. 4, No. 1, pp. A1-A2 (Sep. 2012).
Vozza et al. "Papillomatosis cutis lymphostatica" *Gionale Italiano di Dermatologia e Venereologia*, vol. 144, No. 2, pp. 211-212 (Apr. 2009).
Wojcikowski et al. "Medicinal herbal extracts—Renal friend or foe? Part two: Herbal extracts with potential renal benefits" *Nephrology*, vol. 9, No. 6, pp. 400-405 (Dec. 2004).

* cited by examiner

*Primary Examiner* — Ralph J Gitomer

(74) *Attorney, Agent, or Firm* — Sterne, Kessler, Goldstein & Fox P.L.L.C.

(57) ABSTRACT

The present invention relates to a mixture of active ingredients consisting of *Taraxacum officinalis, Fagopyrum esculentum, Ruscus aculeatus, Solidago virgaurea* and *Orthosiphon stamineus* or extracts of said plants or from said plants and extracts thereof, a composition comprising such a mixture, and uses thereof.

3 Claims, 13 Drawing Sheets

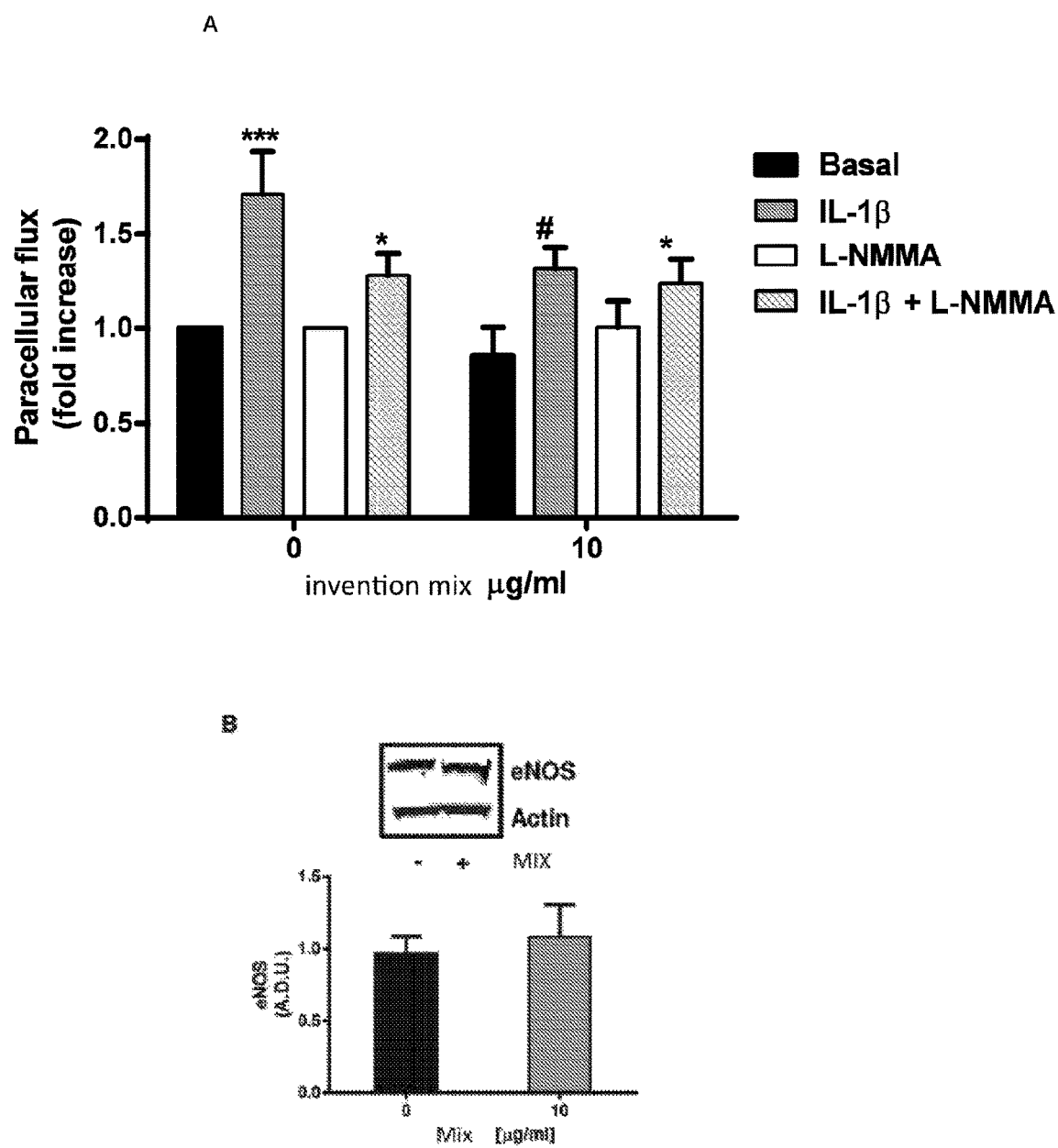
Fig 12 A - B

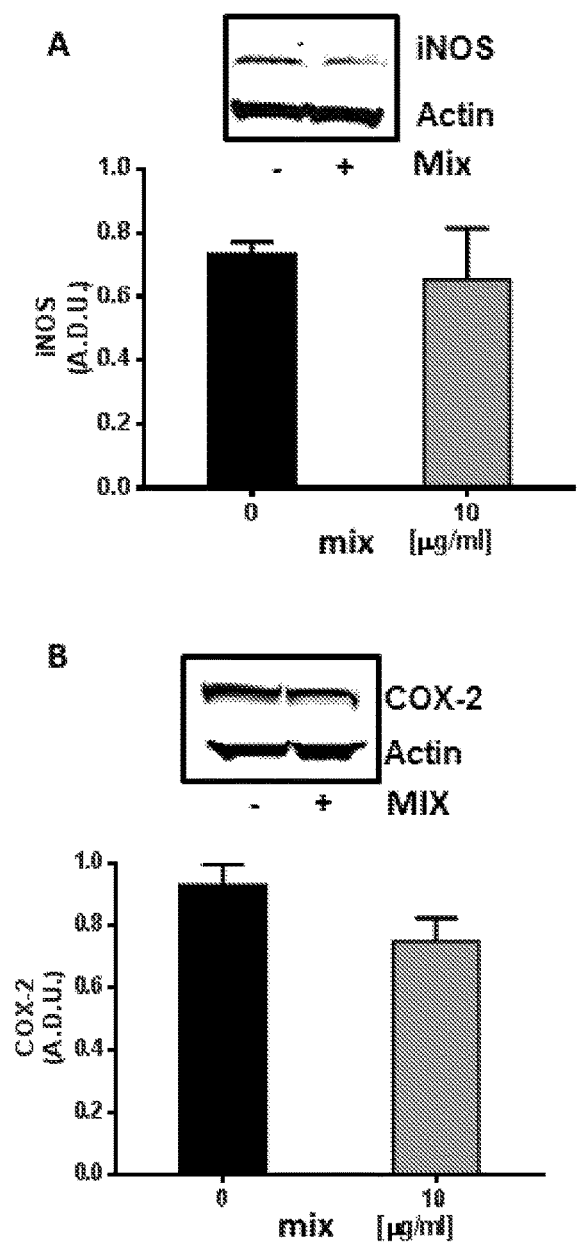
Fig 13 A – B

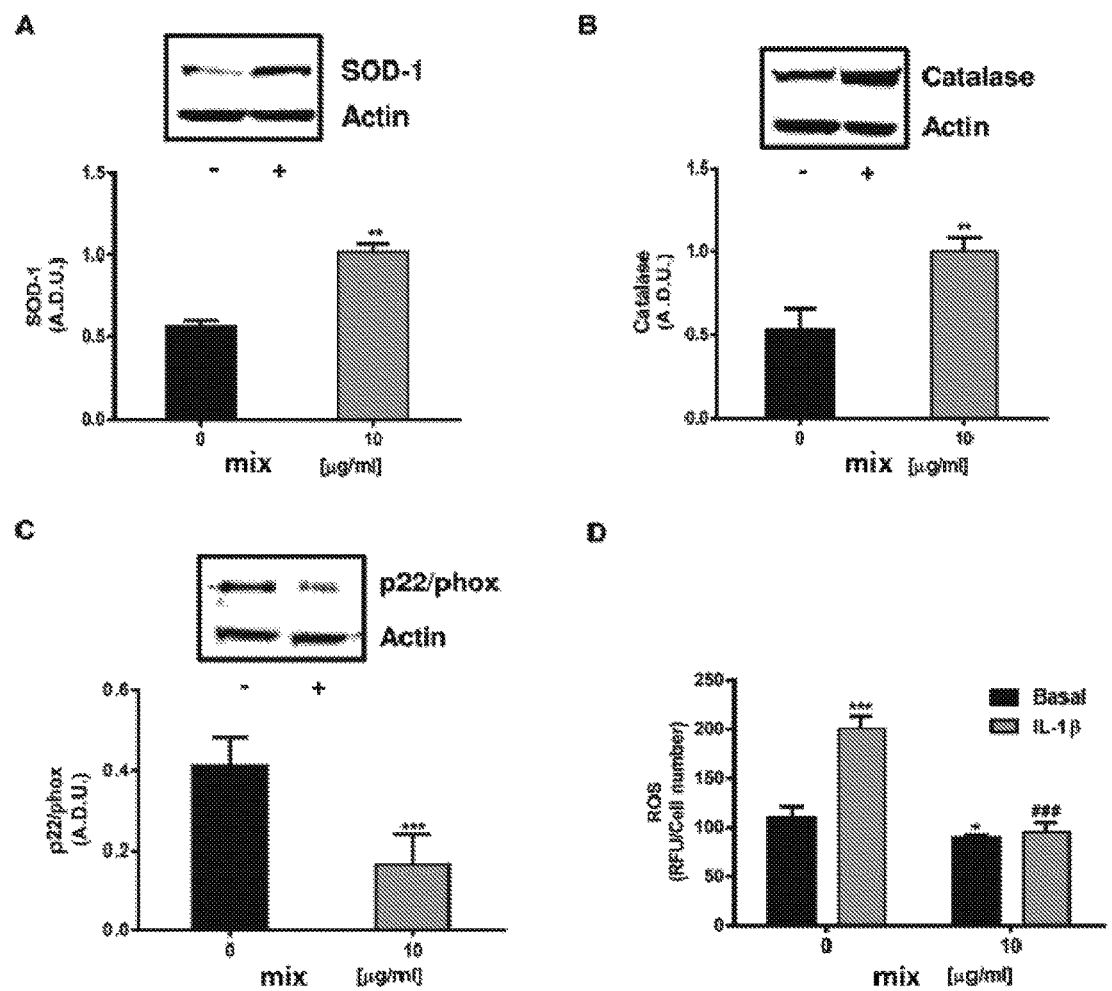
Fig. 14 A-D

METHOD FOR LYMPH DRAINAGE

This application is the U.S. national phase of International Application No. PCT/IB2016/050023, filed 4 Jan. 2016, which designated the U.S. and claims priority to Application No. IT RM2015A000005, filed 7 Jan. 2015; the entire contents of each of which are hereby incorporated by reference.

DESCRIPTION

The present invention relates to a mixture of active ingredients consisting of *Taraxacum officinalis, Fagopyrum esculentum, Ruscus aculeatus, Solidago virgaurea* and *Orthosiphon stamineus* or from extracts of said plants or from said plants and extracts thereof, a composition comprising such a mixture, and uses thereof. The mixture and the composition of the invention promote the depurative physiological process in the body, and are indicated in particular for the treatment of the physiopathology of water retention in obese patients, particularly in order to restore the physiological permeability of the lymphatic endothelium. The invention also relates to uses of the composition of the invention and a treatment of the physiopathology of water retention in obese patients by means of administration of the composition of the invention.

PRIOR ART

The lymphatic system, in addition to maintaining the homeostasis of fluids in tissues, has a key role in immune defence and in the maintenance of the metabolism. It is therefore the interface between the organism and the surrounding environment, forming the physical basis of the immune system, which, by means of its channels and the lymph nodes, carries out the process of presentation and recognition of antigens and activation of the immune response.

The lymphatic system is therefore essential for the immune function, by means of the homeostasis of fluids in the tissues, by means of the absorption of fats in the intestine, and also by means of the removal of fats from the interstices in the majority of tissues.

The lymphatic system enables the absorption of fats originating from the diet, promoting the assimilation (absorption and accumulation) and the metabolism of ingested lipids, at the same time behaving as a sort of "dumping ground" in which the tissues heap dead cells, bacteria, proteins, matrix fragments, lipids and other macromolecules, which will be distributed to the organs intended for removal thereof, such as the liver, kidneys, skin, lungs and large intestine.

The lymphatic system has the following functions:
to maintain and regulate the immune system;
to absorb and re-circulate extracellular fluids in order to maintain the homeostasis of liquids;
to transport macromolecules.

In the human body, water and solutes and, in particular, proteins present in the blood circulation filter through the capillaries to the interstitial space, and in order to balance this flow the interstitial liquid and the proteins present therein re-enter the blood. Each day approximately 50% of the plasma proteins are filtered from the blood capillaries and are not re-absorbed by the venules, but are moved exclusively by the lymphatic system, which has the job of returning them to the systemic circulation. The extravascular accumulation of plasma proteins causes a flow of water from the blood vessel to the interstice, producing oedema. If the lymph present in the thoracic duct were diverted into a suitable receptacle instead of into the systemic circulation, all of the blood would be converted over a short time into lymph. This is life threatening and demonstrates the great importance of the lymphatic system in returning to the blood those proteins and fluids lost from the capillaries.

Interstitial liquid represents, in healthy individuals, approximately 20% of the body weight and is regulated by various temporary mechanisms, including structural changes, adjustment of the forces acting through the vessels (for example osmotic, oncotic and hydrostatic pressure) and the flow of lymph.

In the majority of tissues the lymphatic vessels collect the plasma and the proteins that exit from the blood capillaries. In addition to the fluids and proteins, the lymph in the mesenteric lymph nodes contains fats transported from the lumen of the intestine and collected by the central lymphatic capillaries (initial lymphatic capillaries) located in the intestinal villi.

The concentration of lipids in the intestinal lymph is approximately 1-2% and is highly dependent on the nutritional framework. The flow of intestinal lymph is significantly increased after eating fats. This action can be interpreted as an adjustment to the increased load of lipids and as an aid for leading them through the lymphatic vessels so as to be distributed throughout the body. Recent studies indicate a rise of the contractility of the mesenteric lymphatic vessels in the presence of oxidised low-density lipoproteins (ox-LDL), suggesting a direct effect of the lipids on lymphatic contractility. The mesenteric lymphatic vessels are therefore fundamental for removing the lipids absorbed by the intestine and for maintaining digestive homeostasis.

The rise of fluid in the interstitial space leads to changes, often significant changes, in the architecture of the skin and subcutaneous tissues. As the lymph stasis becomes chronic and due to the resultant oedema, there is a predisposition to have a growing number of fibroblasts, adipocytes and keratinocytes in the oedematous. Such changes in the composition of the tissue lead to a thickening of the skin and fibrosis of the subcutaneous tissue, however these events are not well understood. In the case of lymphedema, i.e. a stage successive to fibrosis, there is inflammation in addition to the lymph stasis and the disturbance of the tissue structure.

Test data recorded in the literature has shown that the loss of lymph in the tissues has an adipogenic and inflammatory effect.

Lymphedema is an accumulation of lymphatic fluid in the interstitial tissues, which causes severe swelling particularly of the extremities, such as the arms and legs, and in rare cases also of other parts of the body. Lymphedema can be primary, that is to say is caused by a change in the lymphatic system itself, or can be secondary to the removal of lymph nodes following surgical interventions, such as a mastectomy, in which, in addition to the removal of the mammary tissue, satellite lymph nodes are also cut away.

In case of severe deterioration of the lymphatic system there is a strong accumulation of lymphatic fluids which will exceed the draining capability of the lymphatic system itself, giving rise to the subsequent recall of fluids rich in proteins which, if untreated, reduces the oxygenation of the tissues, interferes in scarring processes, and can provide terrain for bacterial growth, complicating the clinical picture in lymphangitis.

Lymphedema is different from oedema, which occurs in cases of venous insufficiency, but in this case too can develop into a disorder characterised by combined change of the venous system and also of the lymphatic system, if not correctly treated.

Lymphedema is a pathological condition characterised by the accumulation of fat above all at the lower extremities, and generally manifests itself downwards, that is to say establishes itself from the upper portion of the limbs, i.e. from the hips down, giving rise to the typical appearance of "riding jodhpurs". Lymphedema can become worse with development of oedematous-fibrosclerotic panniculitis up to formation of subcutaneous nodules. In some cases medial adipose deposits can be seen at the knee joint.

Subjects with lymphedema often report that the tissue is painful and susceptible to bruising following small traumas.

A peripheral microangiopathy develops in the lymphedematous tissue and induces a rise of the permeability of the vessels with accumulation of liquid having a high protein content in the extracellular matrix. The accumulation of liquid induces dilation of the pre-lymphatic channels, reducing the outflow thereof. Morphological and functional changes of the lymphatic capillaries are also experienced, for example the formation of micro-aneurysms.

In addition to this, a disturbance of the motor activity of the lymphangion (which represents the anatomofunctional unit of the lymphatic collector, or the segment placed between one valve mechanism and the other) has been observed. The skin tends to lose tone and there is less action with regard to the vessels and the tissue, and in order to increase the interstitial pressure there is a need for a greater quantity of interstitial liquid. In this way the function of drainage of the lymph is also compromised and, as a result, there is a less significant passive mechanism of defence against the development of oedema.

Historical data and recent studies have demonstrated that the lymphatic system and the adipose tissue are anatomically and functionally related.

Lymphatic vascular insufficiency caused by anatomical anomalies, lesions, obstruction or infection gives rise to an accumulation of interstitial fluid and proteins and lipids in the diseased tissue.

In the case of both primary and secondary lymphedema, if not resolved chronic inflammation, fibrosis and accumulation of adipose tissue will set in, and even in the 19$^{th}$ century a German dermatologist affirmed that the stagnation of the fluids in the tissues is able to cause the accumulation of fat. In more recent times, studies on Chy mice have been carried out and have demonstrated that lymph is a potent stimulator of the differentiation of adipocytes and that lymph has a synergic effect with insulin when it comes to promoting adipogenesis. In addition, lymphatic stasis increases the expression of adiponectin, which is known to be increased during the periods of accumulation of fats and decreases during hypertrophy and tissue hypoxia.

The rise of lymphangiogenesis is also associated with inflammatory diseases such as psoriasis and chronic inflammation of the airways:

1—chronic inflammation could promote a rise of the adipose tissue mass for the purpose of satisfying the basic energy need caused by the activation of the immune cells during signalling events and 2—chronic inflammation could promote a greater adipogenesis by means of the stimulation of lymphangiogenesis, worsening the release of lymph in the diseased adipose tissue.

The schema shown in FIG. 10 summarises the problems associated with water retention in obese individuals.

It is clear from the schema that obese subjects tend to accumulate fluids that worsen conditions, resulting in a decrease of the lymphatic drainage and a rise in the permeability of the lymphatic and blood vessels with subsequent deterioration of the extracellular matrix and subsequent inflammation and reduction of excretion of Na+ from the kidneys, also via a compromise of the renin-angiotensin-aldosterone system, present in obese individuals.

Although there are numerous products for the treatment of water retention and of oedema in obese individuals, new compositions that take into account the complex physiopathological picture associated with obesity are desirable.

SUMMARY OF THE INVENTION

The present invention provides a composition that i) acts on the permeability of the blood vessels and of the lymphatic vessels of obese individuals, who therefore present inflammation of such tissues, reducing leakage (i.e. excessive discharge compared with physiological discharge) of the fluids from the lymphatic system and from the circulatory system, thus returning the lymphatic endothelium to a physiological state;

ii) restores a correct channelling in the lymphatic system, allowing a correct reabsorption of the fluids and of the inflammatory molecules therein, consequently also reducing the vicious circle linked with lymphatic adipogenesis;

iii) has a diuretic effect.

The composition of the present invention comprises extracts of plants that, individually, exert some beneficial effects and other negative effects and that, opportunely mixed, are able to exert a general effect that meets the above-mentioned demands.

The authors of the present invention have performed tests on the permeability of the endothelium in order to assess the effects of numerous plant extracts on the permeability of healthy cell cultures of lymphatic cells and blood vessel cells and on cell cultures of lymphatic cells and of blood vessel cells pre-treated with inflammatory agents such as IL-1β in order to mimic the condition of the lymphatic and venous vessels in obese individuals in which there is thus chronic inflammation of such tissues.

The data obtained shows that plants having desirable diuretic effects or effects stimulating the concentration of the lymphangion were not active in restoring the correct permeability of lymphatic cells or of blood vessels pre-treated with IL-1β (i.e. an increase of the permeability of the vessels compared with the physiological permeability observed with such types of cells treated with placebo), meaning that the use of such plants, considered individually, does not meet the above-listed requests.

The authors of the present invention, with the objective of providing a composition which meets the above demands, have identified a group of plants of which the mixed extracts meet the above demands, although extracts of the individual plants instead present effects that do not meet the demands identified above, such as a rise of the permeability of blood and/or lymphatic vessels in cells pre-treated with inflammatory agents such as IL-1β. In the mixture of active ingredients of the present invention, the authors of the present invention were able, by means of opportune mixing, to use some plants for some of the desired effects thereof and to limit the side effects thereof not meeting the demands identified above, thus providing a mixture able to return the lymphatic endothelium damaged by the inflammatory agents to a state of physiological permeability.

The invention thus relates to a mixture consisting of *Taraxacum officinalis, Fagopyrum esculentum, Ruscus aculeatus, Solidago virgaurea* and *Orthosiphon stamineus*, a mixture consisting of extracts of *Taraxacum officinalis, Fagopyrum esculentum, Ruscus aculeatus, Solidago virgaurea* and *Orthosiphon stamineus*, and a mixture consisting of *Taraxacum officinalis, Fagopyrum esculentum, Ruscus aculeatus, Solidago virgaurea* and *Orthosiphon stamineus* and from extracts of *Taraxacum officinalis, Fagopyrum esculentum, Ruscus aculeatus, Solidago virgaurea* and *Orthosiphon stamineus*.

The present invention also relates to a composition comprising, as sole active ingredients, a mixture consisting of *Taraxacum officinalis, Fagopyrum esculentum, Ruscus aculeatus, Solidago virgaurea* and *Orthosiphon stamineus* and at least one vehicle or excipient.

The invention also relates to a composition comprising, as sole active ingredients, a mixture consisting of extracts of *Taraxacum officinalis, Fagopyrum esculentum, Ruscus aculeatus, Solidago virgaurea* and *Orthosiphon stamineus* and at least one vehicle or excipient.

The invention also relates to a composition comprising, as sole active ingredients, a mixture consisting of *Taraxacum officinalis, Fagopyrum esculentum, Ruscus aculeatus, Solidago virgaurea* and *Orthosiphon stamineus* and from extracts of *Taraxacum officinalis, Fagopyrum esculentum, Ruscus aculeatus, Solidago virgaurea* and *Orthosiphon stamineus*.

The invention therefore relates to the use of the mixture or of the composition as defined above and as defined in greater detail hereinafter and in the claims in the treatment of pathologies associated with lymphatic hyperpermeability. In particular, the data obtained and reported demonstrates the suitability of the mixture or of the composition of the invention for use in pathologies associated with lymphatic hyperpermeability that present a deregulation of the integrity of the lymphatic endothelium.

However, the invention also relates to the mixture or the composition as described and claimed here for use in pathologies associated with lymphatic hyperpermeability in which said pathologies are selected from chronic inflammation, lymphedema, lipedema, and water retention pathology, in particular associated with obesity.

In other words, the invention also relates to said mixtures or said compositions for use in the treatment of the lymphatic endothelium subjected to the action of inflammatory agents, moreover in order to return the lymphatic endothelium to its physiological permeability.

The present invention also relates to a method for treating the physiopathology of water retention, in particular associated with obesity, said method comprising the administration, to subjects in need of this, of therapeutically effective amounts of a mixture consisting of *Taraxacum officinalis, Fagopyrum esculentum, Ruscus aculeatus, Solidago virgaurea* and *Orthosiphon stamineus* or extracts thereof, or of said plants and extracts thereof, or of a composition comprising, as sole active ingredients, a mixture consisting of *Taraxacum officinalis, Fagopyrum esculentum, Ruscus aculeatus, Solidago virgaurea* and *Orthosiphon stamineus*, or a mixture consisting of extracts of *Taraxacum officinalis, Fagopyrum esculentum, Ruscus aculeatus, Solidago virgaurea* and *Orthosiphon stamineus* or a mixture consisting of *Taraxacum officinalis, Fagopyrum esculentum, Ruscus aculeatus Solidago virgaurea* and *Orthosiphon stamineus* and extracts of *Taraxacum officinalis, Fagopyrum esculentum, Ruscus aculeatus Solidago virgaurea* and *Orthosiphon stamineus* and at least one pharmaceutically acceptable vehicle and/or excipient.

DETAILED DESCRIPTION OF THE FIGURES

FIG. 1 schematically shows the model used by the authors of the present invention to carry out the permeability test and the study of the effects of the various tested extracts on endothelia of blood or lymphatic vessels in obese individuals (and in individuals in which the blood and lymphatic vessels are subjected to the action of inflammatory agents).

In box A of FIG. 1 what is shown is the model in which lymphatic or hematic endothelial cells are measured in culture on a semi-permeable membrane, with presence of culture medium above and below said membrane, so as to allow the passage of components present in the medium when the cells are not strictly linked to one another, and FITCH-dextran molecules are inserted in the culture medium above the cells.

Quantification by means of fluorescence of the FITC-dextran complex provides a measure of the permeability of the endothelium.

In order to check the activity of the ingredients, once the cells have reached confluence, the medium is removed and the samples (powders, extracts of one of the mixtures) are added and left in contact for 18 hours. Without changing the cell medium, IL1beta (10 ng/ml, 1 h) is added. Once the stimulation time has elapsed, the medium is removed and FITCH-dextran 3 µM is added.

In box B of FIG. 1 it can be seen that the exposure of the endothelial cells to an inflammatory agent, such as IL-1β, induces gaps between the cells with a subsequent rise of the permeability of the endothelium.

In the models of the present invention, cells available commercially from PromoCell, "Human Dermal Lymphatic Endothelial Cells (HDLEC) adult donor" catalogue number C-12217, were used.

FIG. 2 shows the results of the permeability test performed on lymphatic endothelial cells pre-treated with extract of *Fagopyrum esculentum* and then treated with IL1beta. The figure shows how the endothelial cells treated with IL-1β undergo a rise in permeability from 100% (attributed by convention to healthy cells) to approximately 160%, and how the extract alone is able to return the permeability to values close to basal values only at higher tested concentration, demonstrating a weaker protective effect of the mixture of the invention.

FIG. 3 shows the results of the permeability test carried out on lymphatic endothelial cells pre-treated with extract of *Orthosiphon stamineus* and then treated with IL1beta. The figure shows how this extract is the only extract tested able to restore a permeability equal to that of healthy cells by means of a lower concentration, but how with higher concentration it reduces the level of permeability of the cells to below the normal situation (defined, by convention, as 100%), stopping around 80%.

FIG. 4 shows the results of the permeability test carried out on lymphatic endothelial cells pre-treated with extract of *Solidago virgaurea* and then treated with IL1beta. The figure shows how the extract is unable to restore a permeability equal to that of healthy cells and is substantially devoid of any effect on endothelial permeability.

FIG. 5 shows the results of the permeability test carried out on lymphatic endothelial cells pre-treated with co-extract of *Solidago virgaurea* and *Orthosiphon stamineus* (3:1 before co-extraction) and then treated with IL1beta. The figure shows how the co-extract is unable to restore a permeability equal to that of healthy cells and how this co-extract at greater concentration even has an adverse effect on the permeability of the initially inflamed endothelium.

Figure 8:
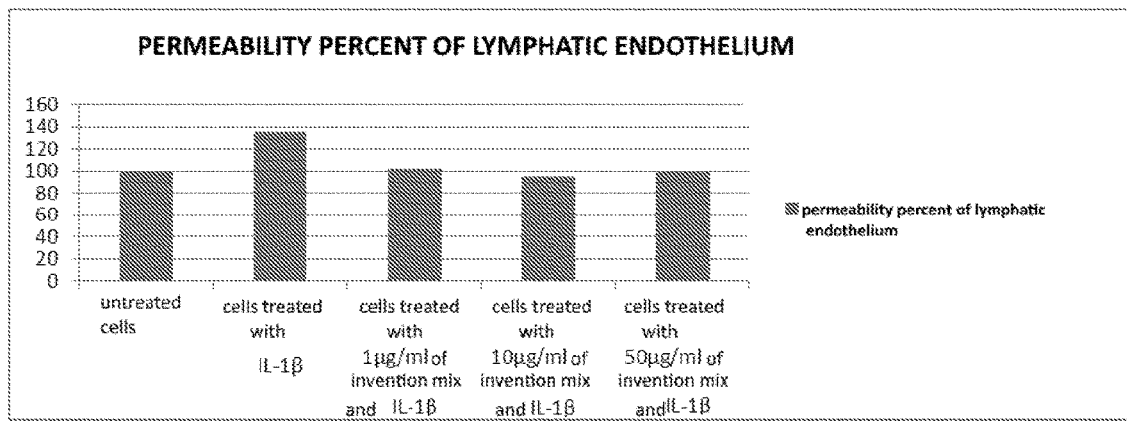
FIG. 8 shows the results of the permeability test carried out on lymphatic endothelial cells pre-treated with the mixture of extracts according to the invention and then treated with IL1beta. The figure shows how the mixture is surprisingly able to restore a permeability equal to that of healthy cells.

FIG. 9 shows the data obtained with tests in triplicate and confirms, in the majority of cases, what already shown in the previous figures, also showing how the results reported in FIG. 8 are significant with respect to the damage caused by the exposure to IL-1β for all the concentrations tested and how the mixture of extracts does not significantly alter the permeability of the healthy cells, either by reduction or increase thereof. In these experiments, in addition to the data concerning the cells treated with IL-1beta and the product to be tested, the data concerning the cells without treatment with IL-1beta, with only the product (extract or mixture of the invention) to be tested, were also analysed.

Figure 6:
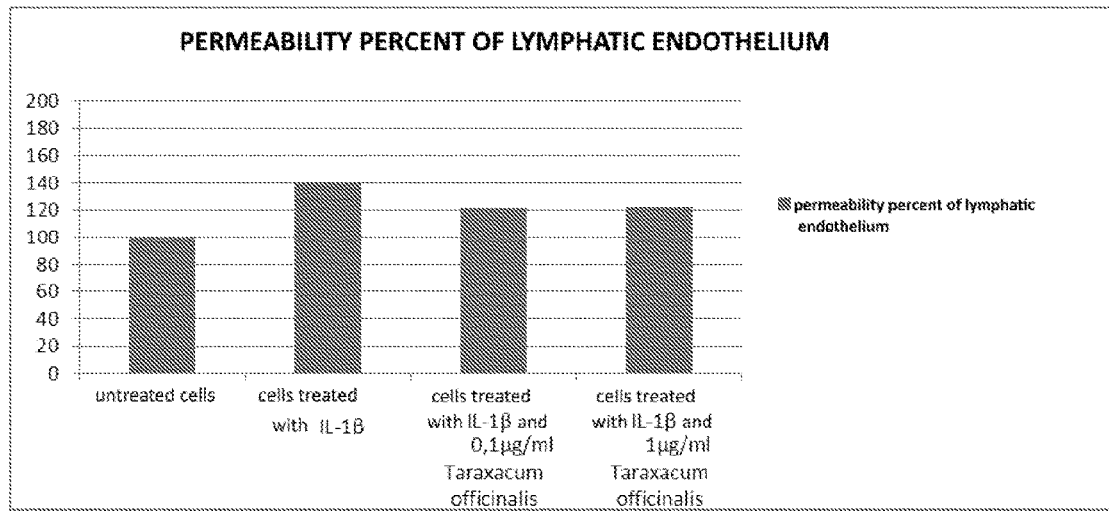
FIG. 6 shows the results of the permeability test carried out on lymphatic endothelial cells pre-treated with extract of *Taraxacum officinalis* and then treated with IL1beta. The figure shows how the extract is unable to restore a permeability equal to that of healthy cells.
Figure 7:
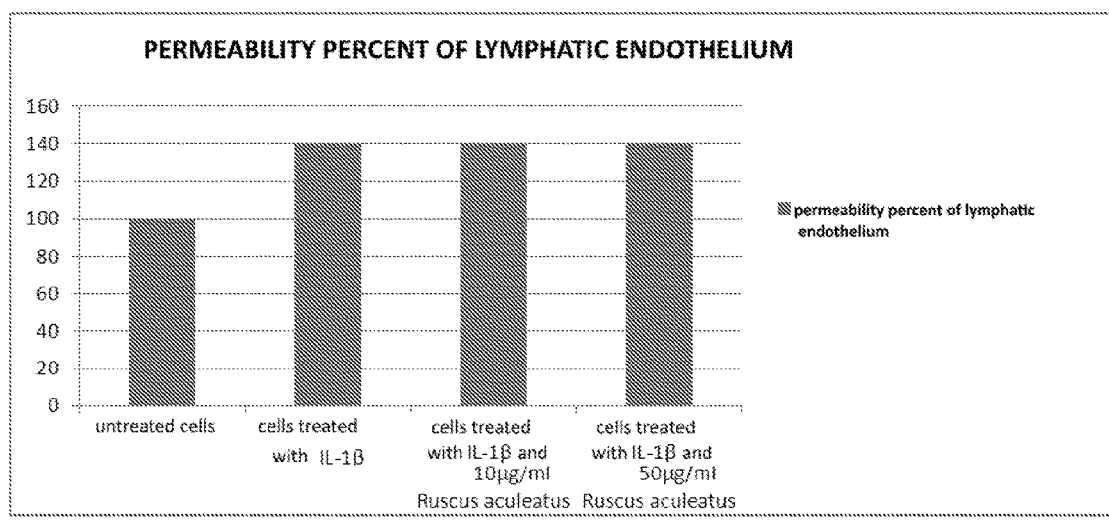
FIG. 7 shows the results of the permeability test carried out on lymphatic endothelial cells pre-treated with extract of *Ruscus aculeatus* and then treated with IL1beta. The figure shows how the extract is unable to restore a permeability equal to that of healthy cells, and how the extract minimally influences the effect of the IL1beta at both concentrations.
Figure 9A:
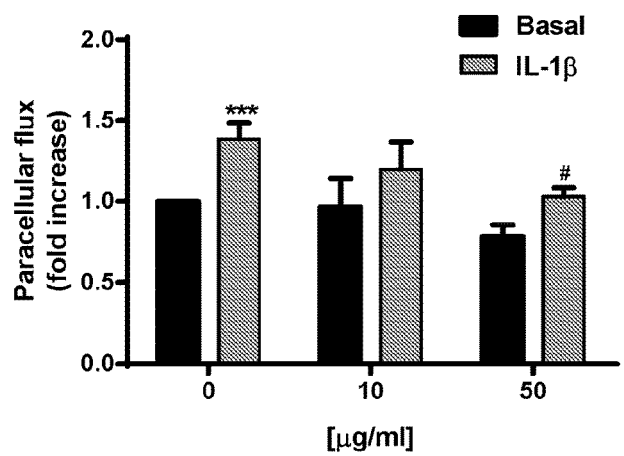
Figure 9B:
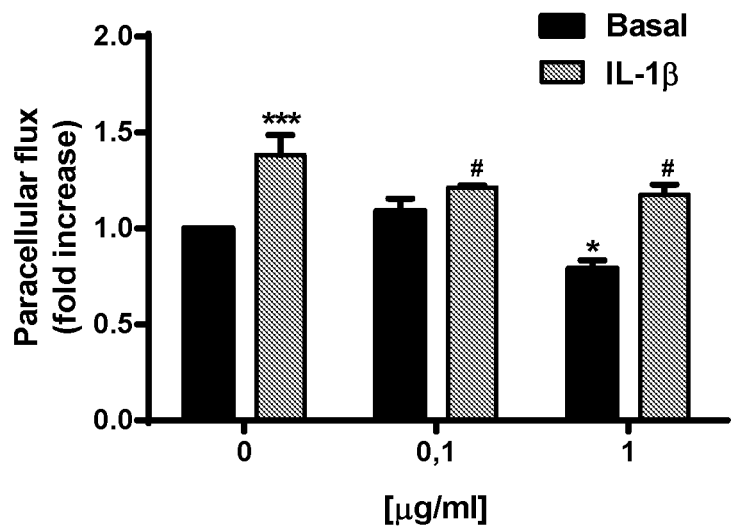
Figure 9C:
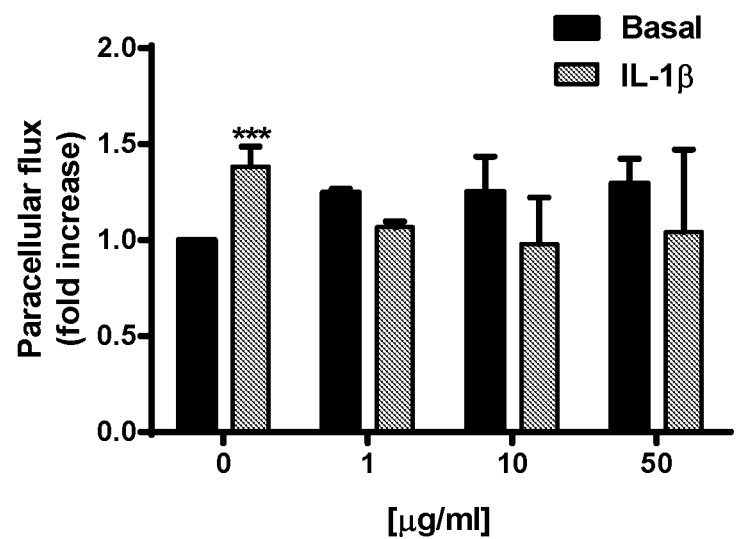

In particular in FIG. 9A the data obtained with HDLEC cells treated with or without IL-1beta and extracts of *Fagopyrum esculentum* are reported. It can be seen from FIG. 9A how the extract is able to restore the permeability to values close to basal values only at the highest tested concentrations, demonstrating a weaker protective effect compared with the mixture of the invention. It would also seem evident, however, that the same concentration has an effect of reduction of the basal permeability on the cells that were not treated with IL-1beta, which is an undesirable effect. FIG. 9B shows the data obtained with *Taraxacum officinalis* (which matches the data in FIG. 6) and also shows an important data, which is that at 1 microgram/ml a significant reduction of the basal permeability is observed, which is an undesirable effect. FIG. 9C shows the data obtained with *Ruscus aculeatus*, demonstrating a reasonable variability of the effect of these extracts on the permeability of the cells, and in any case showing that these extracts are unable to restore, in a statistically significant manner, a permeability such as that of the untreated sample, said data also showing a tendency to increase the permeability of the lymphatic endothelium not subjected to treatment with IL-1beta.

Figure 5:
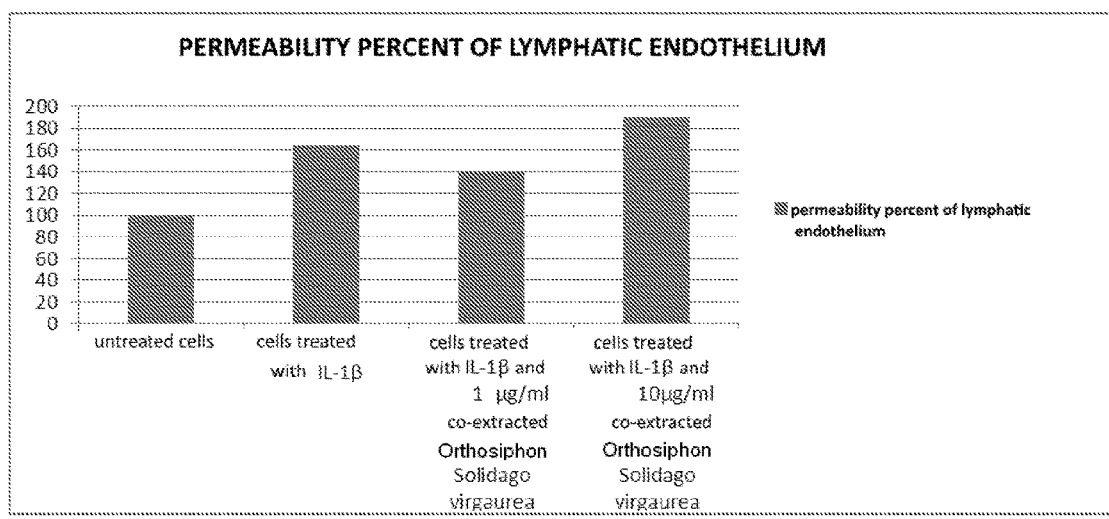
Figure 9D:
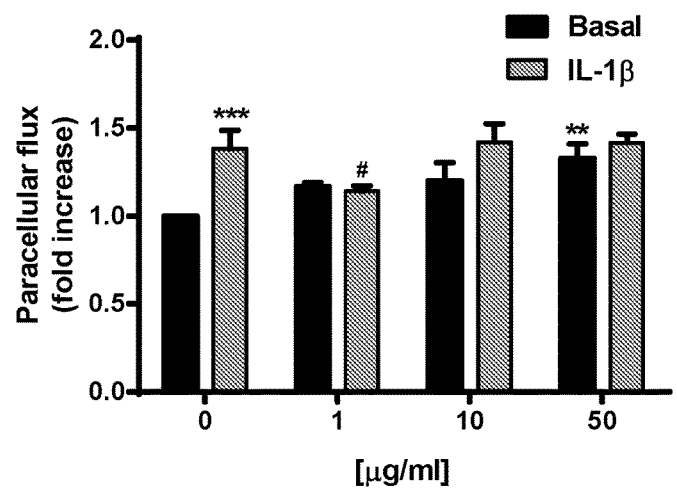

FIG. 9D shows the data obtained with *Solidago virgaurea* and *Orthosiphon stamineus*, in conformity with the data reported in FIG. 5; the figure also shows that such extracts significantly increase the permeability of the lymphatic endothelium not subjected to treatment with IL-1beta, thus creating an undesirable effect.

Figure 9E:
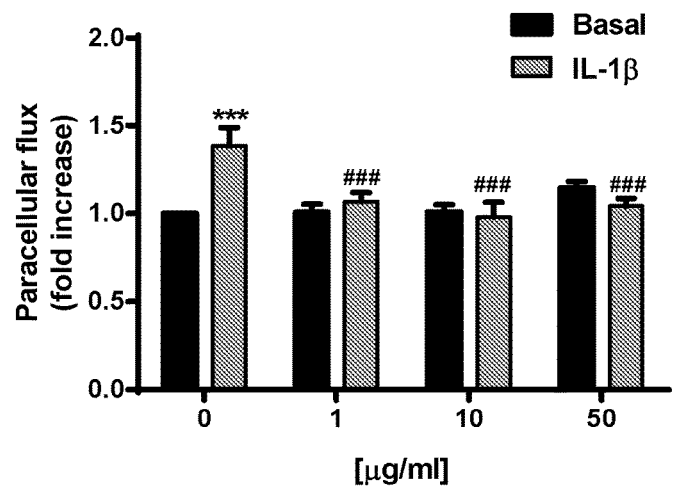
Figure 9F:
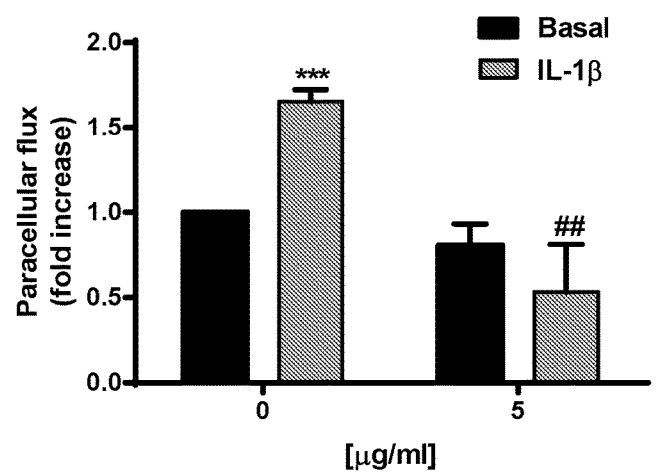
Figure 9G:
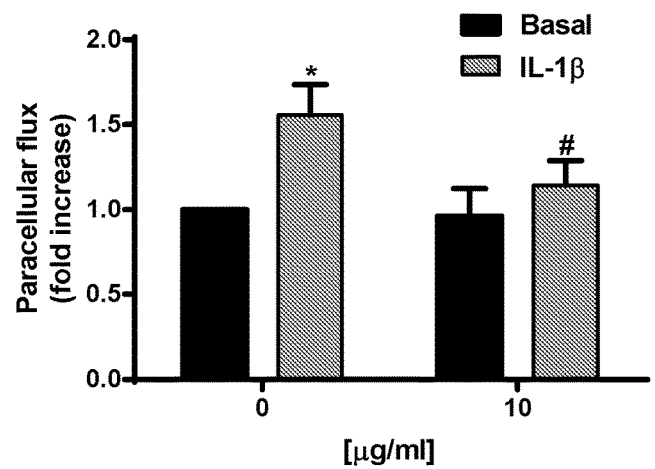

FIG. 9E shows the data obtained with the mixture of the invention, which has the effect of perfectly normalising the permeability of the cells exposed to interleukin, at any tested concentration. The figure also shows how the mixture does not induce practically any variation in the permeability of the lymphatic endothelium treated with the mixture alone. FIG. 9F shows data obtained treating the cells with rutin (5micromilligrams/milliliter) as positive control, and FIG. 9G shows the data obtained treating HDBEC cells with the mixture of the invention, demonstrating a normalising effect of the mixture, even on endothelial cells of blood vessels. The symbol * indicates the basal significance and the symbol # indicates the 0+IL 1beta significance.

Figure 10:
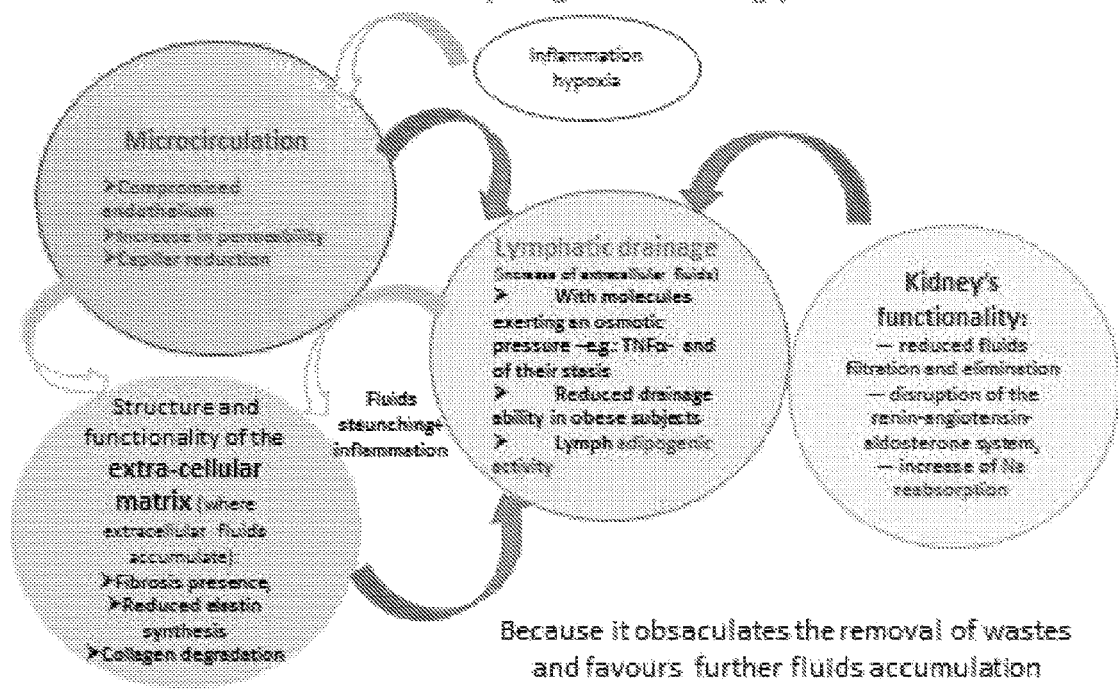

FIG. 10 is a schema that summarises the problems associated with water retention in obese individuals.

Figure 11:
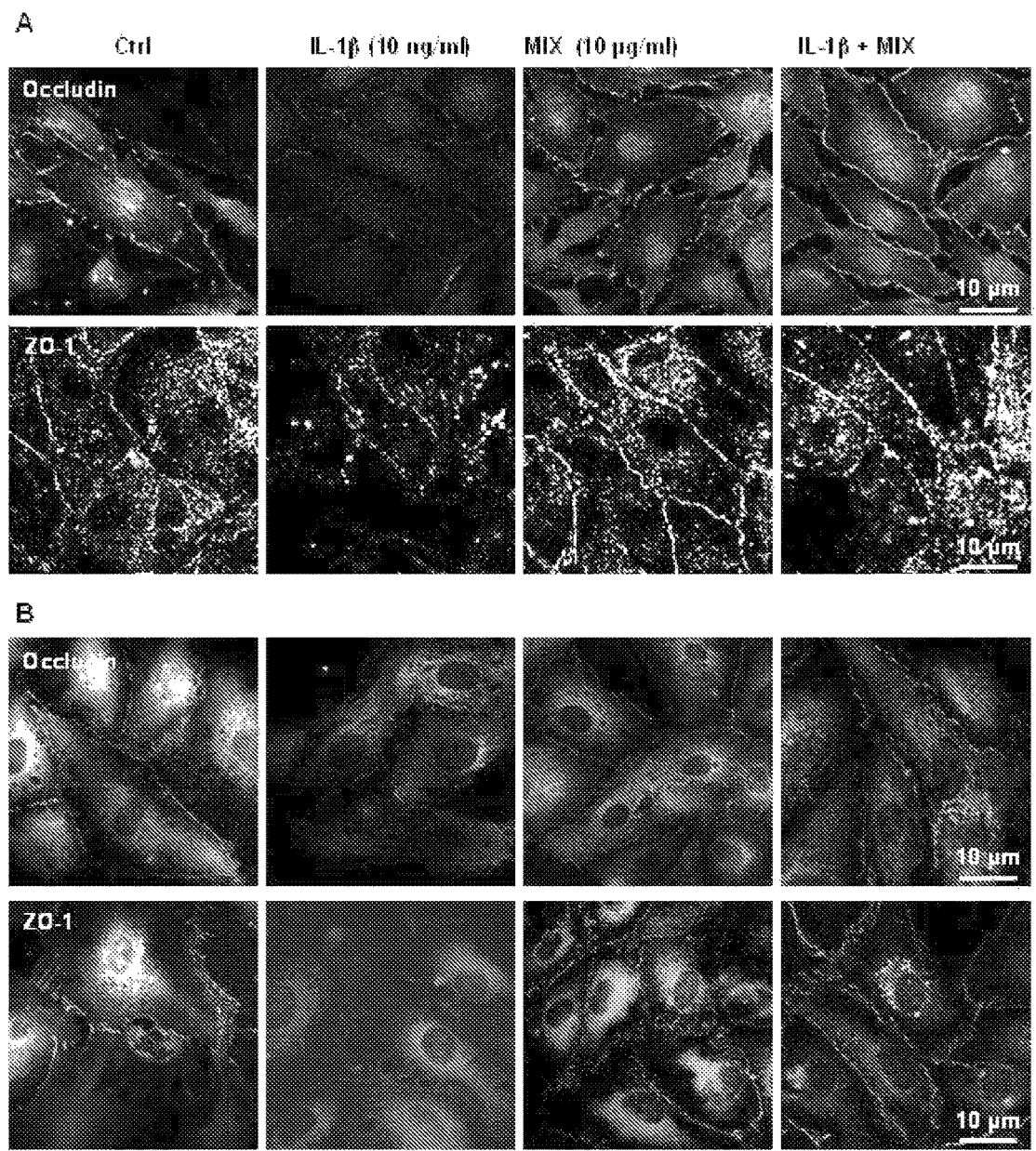

FIG. 11 reports the data of immunofluorescence analyses of occludin (upper boxes) and of the protein ZO-1 (lower boxes) in confluent HDLEC (A) and HDBEC (B) cells treated with the following stimuli: no stimulus, IL-1beta alone (10 ng/ml, 1 hour), mixture of the invention alone (10 micrograms/ml 18 hours); mixture of the invention (18 hours)+IL-1beta (1 hour). The confocal images were taken with 60× enlargement, the scale bar=10 micrometers. Occludin and ZO-1 were assessed as markers representative of tight endothelial junctions. The confluent cells express these markers, whereas they are reduced following treatment with IL-1beta. The pre-incubation with the mixture of the invention shows that this treatment makes it possible to keep the intercellular contacts intact even after treatment with IL-1beta.

FIG. 12 shows the data obtained treating the HDLEC cells with inhibitors of NOS, L-NMMA. FIG. 12A shows the effect on the permeability of the HDLEC cells after treatment with IL-1beta (10 ng/ml 1 hour), with L-NMMA 100 μM and with IL-1beta+L-NMMA with and without the mixture of the invention (10 micrograms/ml 18 hours). FIG. 12B shows the analysis data by means of western blot relative to the production of eNOS in HDLEC cells after exposure to the mixture of the invention (10 micrograms/ml 18 hours). The graphs report the quantification of the protein of interest compared with actin in terms of A.D.U.

FIG. 13 shows the data relating to the production of iNOS and COX-2 (boxes A and B respectively) in HDLEC cells after exposure to the mixture of the invention, A.D.U. still 10 micrograms/ml 18 hours.

FIG. 14 reports in boxes A B and C the data relating to the production of SOD-1, catalase and p22phox respectively, in HDLEC cells after exposure to the mixture of the invention 10 micrograms/ml 18 hours. **P<0.01 compared with basal. The quantification was performed compared with actin and the data are reported in A.D.U. Box D, ROS production in cells stimulated with IL-1beta (10 ng/ml for one hour) with or without the mixture of the invention (10 micrograms/ml 18 hours). The data are expressed as a unit of relative fluorescence (RFU)/number of cells (n=3), *p<0.05 and ***P<0.001 compared with basal. ###P<0.001 compared with IL-1beta. (for all the experiments in FIGS. 12B, 13 and 14 the data is in A.D.U. and n=3).

As mentioned in FIGS. 2 to 9 and 11-14 the result is the result of experiments carried out in triplicate for each tested compound.

Abbreviations Used in the Drawings and in the Text

FBS foetal bovine serum, COX-2 cyclooxygenase 2, e NOS endothelial nitric oxide synthase, HDLEC human dermal lymphatic endothelial cells, HDBEC human dermal blood endothelial cells, i NOS inducible nitric oxide synthase, IL-1β interleukin beta, L-NMMA L-$N^G$-monomethyl arginine, ROS reactive oxygen species, SOD-1 superoxide dismutase 1, TNFα tumour necrosis factor alpha, ZO-1 zona occludens 1.

DETAILED DESCRIPTION OF THE INVENTION

The authors of the present invention have used a cellular model of lymphatic vessels and of blood vessels exposed to inflammatory agents (such as those present in obese individuals produced by inflammatory adipocytes) in order to assess the effects of various plant extracts having desired activities, such as diuretic activities, for example *Taraxacum officinalis, Fagopyrum esculentum*, or activities of induction of the contraction of the base unit of the lymphatic vessels (lymphangion), for example *Ruscus aculeatus*, on the permeability of lymphatic and blood vessels.

It is known in fact that in obese individuals there is observed a rise of the permeability of such vessels with a subsequent non-physiological discharge of liquids from such vessels and an inability thereof to reabsorb and correctly direct the fluids and the inflammatory molecules permeated from the blood and lymphatic vessels, with a subsequent adipogenic effect of the fluids discharged from the lymphatic vessels and the establishment therefore of a vicious circle linked to the physiopathology of water retention associated with obesity.

The authors of the present invention have therefore focused their attention on the effects on the permeability of the lymphatic vessels and blood vessels brought about by plant extracts which are potentially beneficial from the viewpoint of the stimulation of the contraction of the lymphangion (contraction of the lymphatic vessels and possible improvement of the channelling of the lymphatic fluids) or of diuresis.

Figure 1:
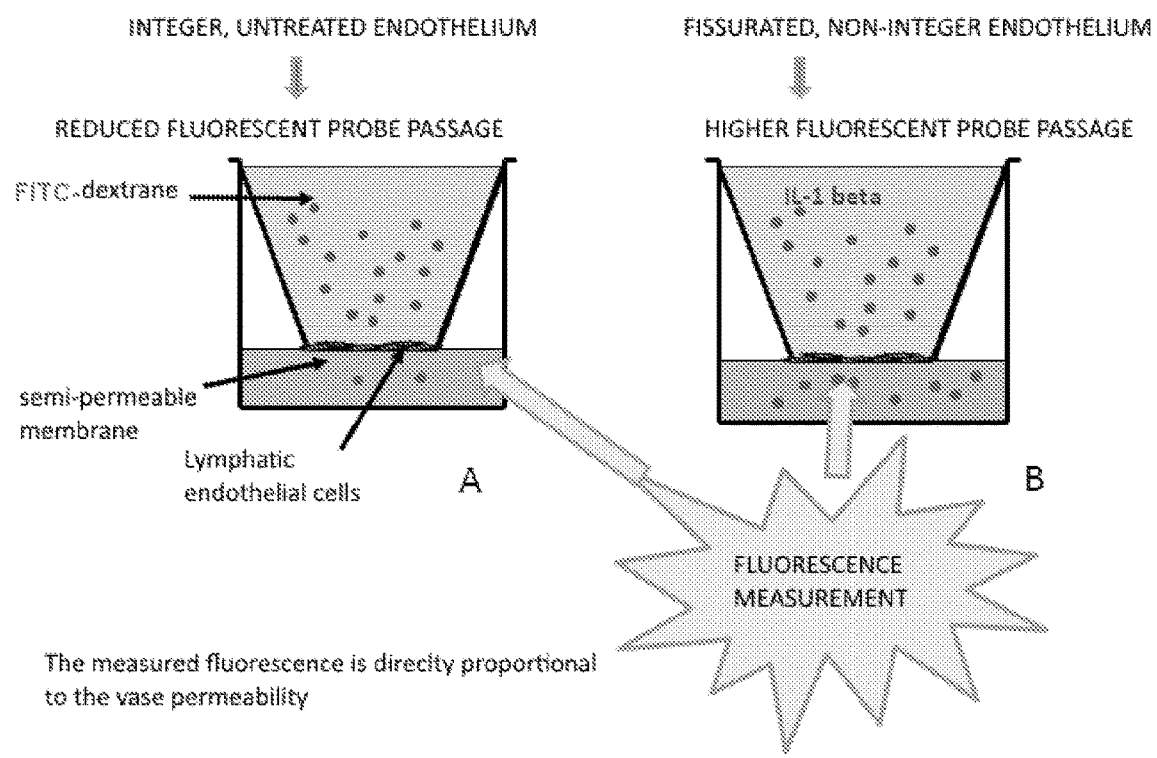
Figure 2:
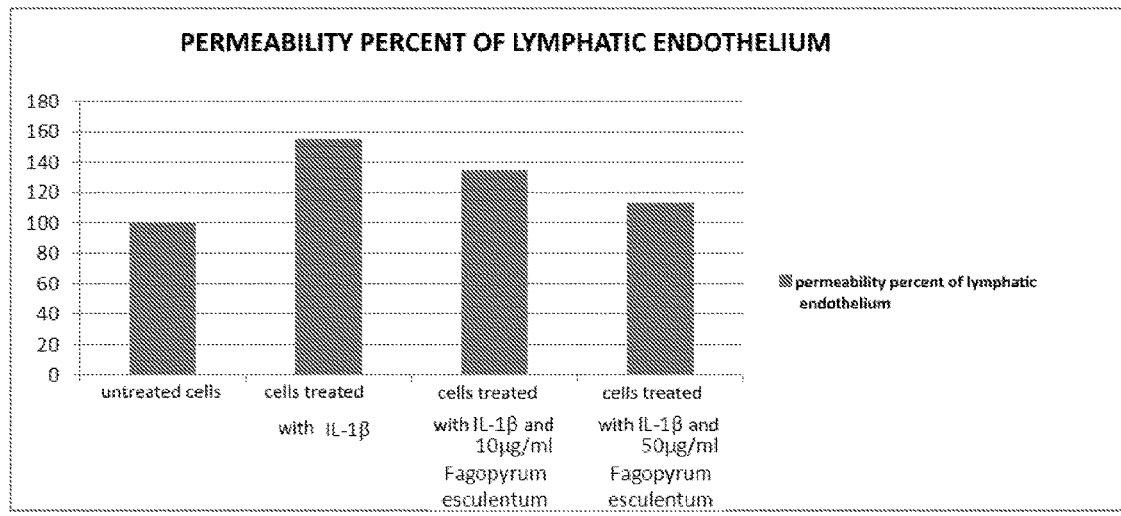
Figure 3:
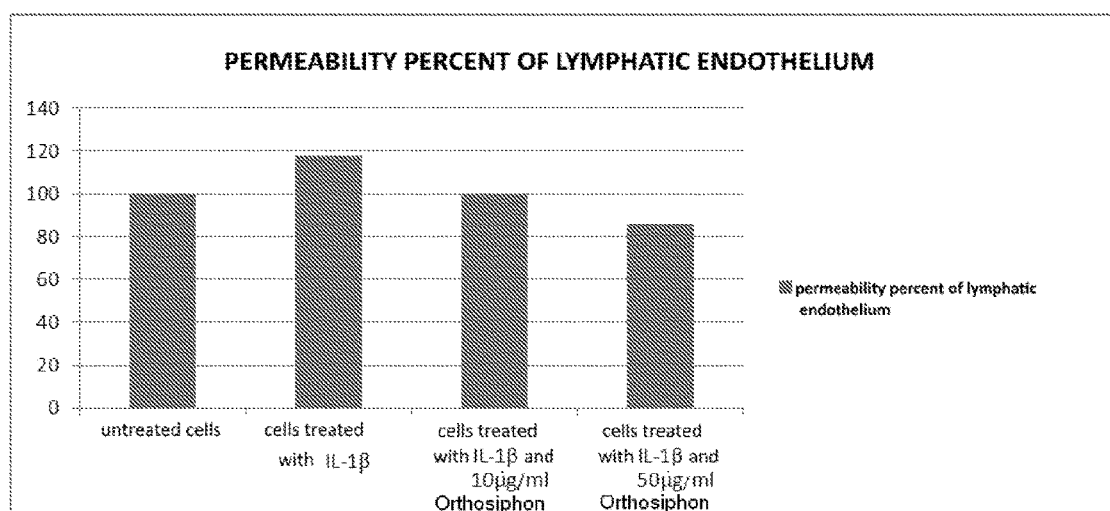
Figure 4:
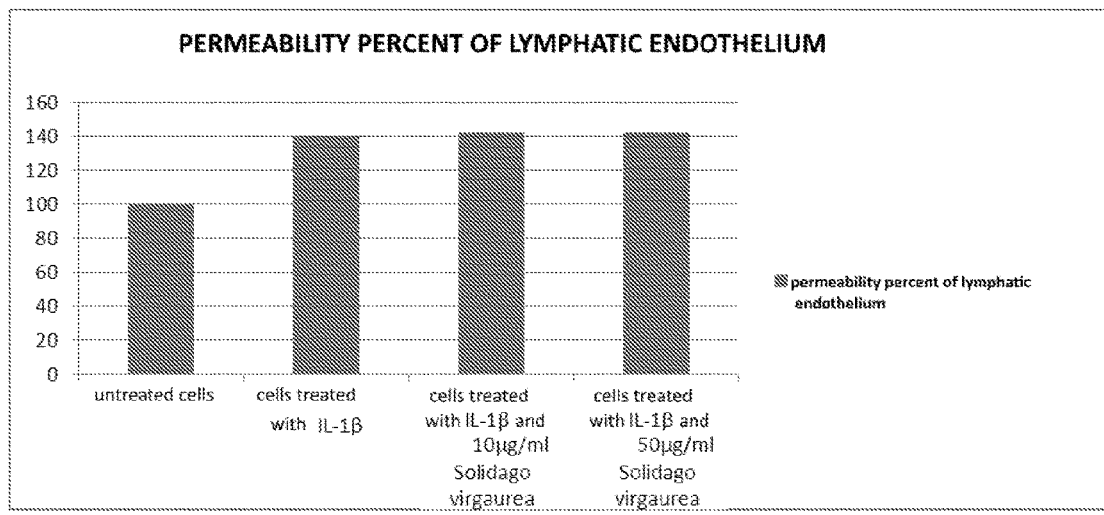

The authors have therefore used a model, shown schematically in FIG. 1, to study the effects of various plant extracts on endothelia of blood or lymphatic vessels. As shown in FIG. 1, the exposure of the endothelial cells to cytokine (as under conditions of inflammation present in obese individuals) changes the integrity of the vascular endothelium, which becomes more permeable to the passage of fluids. The degree of permeability has been determined by way of experiment by measuring the amount of fluorescent probe that crosses the endothelial barrier separating the two compartments representing, respectively, the lumen of the vessel (above the semi-permeable membrane) and the interstice (below the semi-permeable membrane).

Increasing amounts of extracts of various plants were introduced in the medium above the semi-permeable membrane, and the effect thereof on endothelial permeability was examined. The same experiment was performed with the mixture of the invention. Setting as permeability value equal to 100% a value equal to that observed in healthy cells, not exposed to cytokine, it could be seen that only *Ortosiphon stamineus* was successful in reducing the permeability of the lymphatic endothelium at least to 100% at a concentration of 10 µg/ml (FIG. 3), whereas at higher doses this permeability even decreased too much, whereas when co-extracted with *Solidago virgaurea* it had a non-positive effect on the permeability of the lymphatic endothelium (FIG. 5), and that no other single extract is able to return the permeability to 100% (FIGS. 2, 4, 6 and 7). The data obtained by the authors of the present invention shows how, instead, surprisingly, the mixture of the present invention (in which *Ortosiphon stamineus* and *Solidago virgaurea* are present also as co-extracts) is able to return the lymphatic endothelial permeability to 100% at any tested concentration (FIG. 8 and FIG. 9E).

In other words, the authors of the invention have demonstrated that the mixture of the invention is able to reduce the hyperpermeability of the lymphatic endothelium at any tested concentration in a manner superior to that of any component tested individually, indicating that the selected combination protects the correct permeability of the lymphatic endothelium optimally and in a constant manner. The authors have also demonstrated how, in contrast to the majority of single extracts, the mixture of the invention does not bring about any modifications in the lymphatic endothelial permeability in the absence of the cytokine inflammatory agent, indicating how such a mixture therefore would not have undesirable side effects on healthy endothelia.

The authors of the present invention have also found that the co-extraction of *Ortosiphon stamineus* and *Solidago virgaurea* provides a co-extract having better diuretic activities compared with those resulting from a simple addition of the single extracts of the two plants.

In addition, the authors of the invention have demonstrated that the mixture selected by them, as described and claimed here, provides its effect on cellular permeability by promoting the integrity of the tight junctions, and that said mixture also reduces the expression of inflammatory elements, such as inducible nitric oxide synthase (i NOS) and cyclooxygenase 2 (COX-2), without changing the endothelial NOS (e NOS), demonstrating therefore how the mixture is also useful in improving modified lymphatic circulation conditions and in supporting the physiological functionality of the lymphatic endothelium.

The selection of extracts performed by the authors of the present invention thus provides a mixture that therefore satisfies all the requests listed below, that is to say it i) acts on the permeability of the blood vessels and of the lymphatic vessels of obese individuals, who therefore present inflammation of such tissues, reducing leakage (that is to say excessive discharge compared with physiological discharge) of the fluids from the lymphatic system and from the circulatory system;

ii) restores a correct channelling in the lymphatic system, allowing a correct reabsorption of the fluids and of the inflammatory molecules therein, subsequently also reducing the vicious circle associated with lymphatic adipogenesis;

iii) has a diuretic effect and at the same time does not have the undesirable side effects associated with the single extracts of the plants that form the mixture of the present invention, particularly with regard to the permeability of the lymphatic endothelium.

The present invention thus relates to a mixture consisting of *Taraxacum officinalis, Fagopyrum esculentum, Ruscus aculeatus, Solidago virgaurea* and *Orthosiphon stamineus* or a mixture consisting of extracts of said plants or a mixture consisting of said plants and from extracts of said plants.

For the purposes of the present invention the term *Taraxacum officinalis* means the roots of said plant or the term extract of *Taraxacum officinalis* means a hydroalcoholic extract (such as ethanol/water 40-70%, for example 60%) of roots of *Taraxacum officinalis*.

For the purposes of the present invention the term *Fagopyrum esculentum* means the leaves of said plant or the term extract of *Fagopyrum esculentum* means a hydroalcoholic extract (such as ethanol/water 40-80%, for example 70%) of leaves of *Fagopyrum esculentum*.

For the purposes of the present invention the term *Solidago virgaurea* means the tops of said plant or the term extract of *Solidago virgaurea*, means an extract (such as ethanol/water 30-60%, for example 40%) of tops of *Solidago virgaurea*.

For the purposes of the present invention the term *Orthosiphon stamineus* means the leaves of said plant or the term extract of *Orthosiphon stamineus*, means an extract (such as ethanol/water 40-70%, for example 50%) of leaves of *Orthosiphon stamineus*.

For the purposes of the present invention the term *Ruscus aculeatus* means the root stock and/or roots of said plant or the term extract of *Ruscus aculeatus*, means an extract (such as ethanol/water 40-80%, for example 70%) of root stock or root of *Ruscus aculeatus*.

The parts of the plant can be fresh or dried.

For the purposes of the present invention the term co-extract of *Solidago virgaurea* and *Orthosiphon stamineus* means an extract of the tops of *Solidago virgaurea* and of leaves of *Orthosiphon stamineus* produced by placing the suitable parts of each plant in the same solvent, for example leaves of *Solidago virgaurea* and leaves of *Orthosiphon* in a ratio of 1:1 or 2:1 or of 3:1 and proceeding with the extraction in accordance with standard methodology so as to obtain a hydroalcoholic extract (such as ethanol/water 40-70%, for example 50%).

Each of the above-mentioned extracts can be in lyophilised form.

In a preferred embodiment the invention relates to a mixture consisting of extracts of *Taraxacum officinalis, Fagopyrum esculentum, Ruscus aculeatus Solidago virgaurea* and *Orthosiphon stamineus*, in another embodiment the invention relates to a mixture consisting of *Taraxacum officinalis, Fagopyrum esculentum, Ruscus aculeatus, Orthosiphon stamineus*, and *Solidago virgaurea*, and in yet another embodiment the invention relates to a mixture consisting of *Taraxacum officinalis, Fagopyrum esculentum, Ruscus aculeatus Solidago virgaurea* and *Orthosiphon stamineus* and from extracts of *Taraxacum officinalis, Fagopyrum esculentum, Ruscus aculeatus, Orthosiphon stamineus*, and *Solidago virgaurea* in which all three mixtures are for use in the treatment of pathologies associated with lymphatic hyperpermeability. In particular, the data obtained and reported shows the suitability of the mixture of the invention for use in pathologies associated with lymphatic hyperpermeability, in particular for pathologies that present a deregulation of the integrity of the lymphatic endothelium and that can be selected, for example, from chronic inflammation, lymphedema, lipedema, and water retention physiopathology, in particular in cases in which said physiopathology is associated with circulatory stasis, lymphedema, and/or inflammation of the tissues, for example in obese individuals. In one embodiment of the invention the mixture is intended for use in the treatment of the lymphatic endothelium subjected to the action of inflammatory agents so as to return said endothelium to a state of permeability similar or equal to that of healthy (physiological) lymphatic endothelium.

In accordance with the present invention, when reference is made to the fact that a certain component consists of from x % to y % of the mixture of the invention, this means that said component consists of from x % to y % by weight of the mixture of the invention, preferably dry weight.

In one embodiment *Taraxacum officinalis* consists of from 12% to 33% of the mixture of the invention *Ruscus aculeatus* consists of from 6% to 25% of the mixture of the invention, and *Solidago virgaurea* and *Orthosiphon* consist of, on the whole, from 35% to 55% of the mixture of the invention.

*Solidago virgaurea* e *Orthosiphon stamineus* are preferably in a ratio of 1:1, 2:1 or of 3:1 or of 4:1, more preferably in a ratio of 3:1.

In one embodiment of the invention said extract of *Taraxacum officinalis* consists of from 23% to 33% of the mixture of the invention, said extract of *Fagopyrum esculentum* consists of from 12 to 25% of the mixture of the invention, said extract of *Ruscus aculeatus* consists of from 6% to 12% of the mixture of the invention, and said extracts of *Solidago virgaurea* and *Orthosiphon* consist of, on the whole, from 35% to 55% of the mixture of the invention. In a preferred embodiment of the invention the extract of *Solidago virgaurea* and *Orthosiphon stamineus* is provided by placing the suitable parts of each plant in the same solvent, for example leaves of *Solidago virgaurea* and leaves of *Orthosiphon stamineus* in a ratio of 1:1, 2:1 or of 3:1 and by proceeding with the extraction in accordance with standard methodology as described above. In this case the extract as described is also defined here, in the present invention, as co-extract of *Solidago virgaurea* and *Orthosiphon stamineus*.

However, in one embodiment of the invention said extract of *Taraxacum officinalis* consists of from 23% to 33% of the mixture of the invention, said extract of *Fagopyrum esculentum* consists of from 12 to 25% of the mixture of the invention, said extract of *Ruscus aculeatus* consists of from 6% to 12% of the mixture of the invention, and said extracts of *Solidago virgaurea* and *Orthosiphon stamineus* are in the form of a co-extract forming from 35% to 55% of the mixture of the invention.

In a further embodiment the active ingredients may comprise the mixture of plants as indicated above and the mixture of extracts as indicated above.

In accordance with the present description, the values indicated as a percentage range include, precisely, all whole numbers and all decimals from one end to the other of the range, inclusive of extremes. Thus, when reference is made in the present description of the invention to "from 23% to 33%", this means at any point of the description and in any embodiment of the mixture or of the composition comprising the mixture: 23%; 23.5%; 24%; 24.5%; 25%; 25.5%; 26%; 26.5%; 27%; 27.5%; 28%; 28.5%; 29%; 29.5%; 30%; 30.5%; 31%; 31.5%; 32%; 32.5%; 33%; and also the other decimals comprised therebetween.

Similarly, when reference is made in the present description of the invention to "from 12% to 25%", this means at any point of the description and in any embodiment of the mixture or of the composition comprising the mixture: 12%; 12.5%; 13%; 13.5%; 14%; 14.5%; 15%; 15.5%; 16%; 16.5%; 17%; 17.5%; 18%; 18.5%; 19%; 19.5%; 20%; 20.5%; 21%; 21.5%; 22%; 22.5%; 23%; 23.5%; 24%; 24.5%; 25% and also the other decimals comprised therebetween.

When reference is made in the present description of the invention to "from 6% to 12%", this means at any point of the description and in any embodiment of the mixture or of the composition comprising the mixture: 6%; 6.5%; 7%; 7.5%; 8%; 8.5%; 9%; 9.5%; 10%; 10.5%; 11%; 11.5%; 12%; and also the other decimals comprised therebetween.

Lastly, when reference is made in the present description of the invention to "from 35% to 55%, this means at any point of the description and in any embodiment of the mixture or of the composition comprising the mixture: 35%; 35.5%; 36%; 36.5%; 37%; 37.5%; 38%; 38.5%; 39%; 39.5%; 40%; 40.5%; 41%; 41.5%; 42%; 42.5%; 43%; 43.5%; 44%; 44.5%; 45%; 45.5%; 46%; 46.5%; 47%; 47.5%; 48%; 48.5%; 49%; 39.5%; 50%; 50.5%; 51%; 51.5%; 52%; 52.5%; 53%; 53.5%; 54%; 54.5%; 55 and also the other decimals comprised therebetween.

The present invention, as already mentioned, also relates to a composition comprising, as sole active ingredients, a mixture, in accordance with any one of the embodiments described above, consisting of extracts of *Taraxacum officinalis*, *Fagopyrum esculentum*, *Ruscus aculeatus*, *Orthosiphon stamineus* and *Solidago virgaurea* and at least one vehicle or excipient, in an alternative embodiment the present invention also relates to a mixture consisting of *Taraxacum officinalis*, *Fagopyrum esculentum*, *Ruscus aculeatus*, *Orthosiphon stamineus* and *Solidago virgaurea* and at least one vehicle or excipient, and in a further embodiment the present invention relates to a mixture consisting of *Taraxacum officinalis*, *Fagopyrum esculentum*, *Solidago virgaurea*, *Orthosiphon stamineus* and *Ruscus aculeatus* and extracts of *Taraxacum officinalis*, *Fagopyrum esculentum*, *Solidago virgaurea*, *Orthosiphon stamineus* and *Ruscus aculeatus*.

Such a composition therefore comprises, as sole active ingredients, the plants or extracts that form the mixture of the invention, and also in the composition of the invention the extract of *Orthosiphon stamineus* and *Solidago virgaurea* may be in the form of a co-extract.

As described above for the mixture, the composition of the invention is suitable for use in the treatment of pathologies associated with lymphatic hyperpermeability. In particular, the data obtained and reported shows the suitability of the mixture of the invention for use in pathologies associated with lymphatic hyperpermeability, in particular for pathologies that present a deregulation of the integrity of the lymphatic endothelium and that can be selected, for example, from chronic inflammation, lymphedema, lipedema, and water retention physiopathology, in particular in cases in which said physiopathology is associated with circulatory stasis, lymphedema, and/or inflammation of the tissues, for example in obese individuals.

In one embodiment of the invention the composition as described and claimed is therefore suitable for use in the treatment of the physiopathology of water retention associated with obesity. The composition of the invention, similarly to the mixture of the invention, is aimed in particular at overweight/obese individuals who wish to assist the physiological process of weight loss by rebalancing the correct functionality of the processes of tissue drainage and in particular of the lymphatic system involved in the water retention physiopathology linked to obesity caused also by inflammation of the lymphatic endothelium and by the increase of permeability thereof caused by the fissuration (hyperpermeability) thereof as a result of inflammatory agents.

The composition according to the invention may be, for example, a phytopharmaceutical composition, a food for special medical purposes, or a dietary supplement.

In accordance with the invention the composition of the invention may therefore be a composition in which said extract of *Taraxacum officinalis* consists of from 23% to 33% of the mixture of active ingredients, said extract of *Fagopyrum esculentum* consists of from 12 to 25% of the mixture of active ingredients, said extract of *Ruscus aculeatus* consists of from 6% to 12% of the mixture of active ingredients, and said extracts of *Solidago virgaurea* and *Orthosiphon* consist of, on the whole, from 35% to 55% of the mixture of active ingredients. As already mentioned above, said extracts of *Solidago virgaurea* and *Orthosiphon* can be in the form of a co-extract forming from 35% to 55% of the mixture of the invention.

Still in accordance with the invention, the composition may be a composition in which said *Taraxacum officinalis* consists of from 12% to 33% of said mixture, said *Fagopyrum esculentum* consists of from 12 to 25% of said mixture, said *Ruscus aculeatus* consists of from 6% to 25% of said mixture, and said *Solidago virgaurea* and *Orthosiphon stamineus* consist of, on the whole, from 35% to 55% of said mixture.

In a preferred embodiment said composition is suitable for oral administration and is in the form of a fluid, herb tea, decoction, macerated material, suspension, solution, granulate, powder, tablet, operculum, solid gelatin, soft gelatin.

In accordance with a further embodiment, the composition of the invention is suitable for topical use and may therefore be in the form of a fluid, vaporisable solution, cream, ointment, gel, or emulsion.

In accordance with the present invention one or more of the following ingredients can be used as excipients and/or vehicles: natural gums, such as gum arabic, guar gum, xanthan gum; natural and artificial sweeteners (honey, brown sugar and refined sugar); polysaccharides (cellulose, rice starch, potato starch, corn starch); natural waxes, including carnauba wax, beeswax, natural oils such as sweet almond oil, sunflower oil, emulsions of natural origin (sucrose esters, esters of stearic acid), and any other excipient that could be chosen from the prior art by a person skilled in the art without exercising inventive skill.

In addition, the composition of the invention, in accordance with any one of the described embodiments, may also comprise at least one neutral flavouring and/or natural preservative.

Said natural flavouring and/or said natural preservative can be any natural flavouring and/or preservative known to a person skilled in the art to be suitable for providing compositions for oral use, and could be selected for example, but with no limitation, from natural orange flavouring, natural blackberry flavouring, liquorice extract, orange peel, orange juice, tangerine juice, juice, grape juice, blackberry juice, elderflower juice, blueberry juice, pineapple juice, grapefruit juice, currant juice, raspberry juice, apple juice, lemon juice.

That which has been described thus far for the mixture of the invention clearly therefore applies, mutatis mutandis, for the composition of the invention.

EXAMPLES AND METHODS

Non-limiting examples of embodiments of the composition of the invention and of suitable dosages for administration thereof will be provided here.

1. Composition Example 1

Fluid, single dose approx. 10-20 grams

| component | % |
| --- | --- |
| NATURAL FLAVOURINGS/PRESERVATIVES | 93.2-96.3% |
| CO-EXTRACT *Solidago virgaurea Orthosiphon* | 1.5-2.5% |
| *Fagopyrum esculentum* lyophilised leaf extract | 1-1.5% |
| *Ruscus aculeatus* lyophilised root extract | 0.2-0.8% |
| *Taraxacum officinalis* lyophilised root extract | 1-2% |
| TOTAL | 100 |

The natural flavourings and/or preservatives in the composition above can be, for example, one or more from orange juice, grape juice, apple juice, lemon juice (optionally one or more of said juices can be concentrated), natural flavouring in the form of orange powder, blackberry powder, lemon powder, tangerine powder, citrus powder, pineapple powder, strawberry powder, cherry powder, blackberry, mixed berry powder.

The daily dose for such a product is equal to 10-20 grams.

Alternatively, the above-described composition may comprise a mixture of an extract of *Solidago virgaurea* and an extract of *Orthosiphon stamineus* in a ratio of approximately 3:1.

2. Composition Example 2

Prepared by infusion with roughly chopped parts of used plants, 1.5-2.5 g of single dose.

| component | % |
|---|---|
| *Fagopyrum esculentum* roughly chopped leaf | 7-17 |
| *Solidago virgaurea* roughly chopped top | 7-17 |
| Orthosiphon roughly chopped leaf | 15-30 |
| *Taraxacum officinalis* roughly chopped root | 5-25 |
| *Ruscus aculeatus* roughly chopped root | 3-20 |
| Excipients and natural flavourings/preservatives | 1-50 |
| TOTAL | 100 |

Composition 2 may optionally comprise approximately from 2% to 8% of a mixture of extracts according to the present description.

The natural flavourings and/or preservatives in the composition above can be, for example, one or more from orange peel, liquorice roots, lemon peel.

The daily does for such a product is equal to 1.5-2.5 grams.

3. Composition Example 3

In the form of an oral solid (powder, granulate, capsule, tablet), 80-100 mg of single dose.

| article description | % |
|---|---|
| *Fagopyrum esculentum* lyophilised leaf extract | 10-15 |
| COEXTR. *Solidago virgaurea* - Orthosiphon lyophilised co-extract | 20-25 |
| *Taraxacum officinalis* lyophilised root extract | 12-18 |
| *Ruscus aculeatus* lyophilised root extract | 3-8 |
| Excipients and natural flavourings/preservatives | 34-45 |
| TOTAL | 100 |

The natural flavourings and/or preservatives in the composition above can be, for example, one or more from natural flavouring in the form of orange powder, blackberry powder, lemon powder.

The daily dose for such a product is equal to 1.0-1.4 grams

The data obtained in the experiments reported below and shown in the figures shows how, in addition to maintaining the correct permeability, the treatment of the lymphatic endothelium with the mixture of the invention positively regulates all the characteristics providing protection of the endothelium, whilst the key enzymes involved in cellular damage and in activation towards an inflammatory phenotype are sub-regulated by the mixture, thus preparing the lymphatic endothelium to react to the inflammatory attack.

4. Vascular Permeability Test

Materials and Methods in Detail

Cell Cultures

Lymphatic endothelial cells (derma) and blood vessels obtained from commercial sources (available from Promo-Cell, Germany "Human Dermal Lymphatic Endothelial Cells (HDLEC)" and "Human Dermal Blood Endothelial Cells (HDBEC)") were used. The cells were cultivated and kept in culture as recommended by the vendor with FBS 10% in complete endothelial cell basal medium MV2 (Promocell, Heidelberg, Germany) at 37° C. in $CO_2$ 5% and divided 1:3 twice a week up to the 10th time.

Treatment

The samples were assessed in 2-3 concentrations vs. vehicle alone on the cell cultures, untreated and treated with IL1beta (10 ng/ml), to understand if they have any effect in themselves on undamaged cells and if the tested substances are able to reverse the rise in permeability induced by IL1beta.

Thus, for each cell culture and each extract, the points to be assessed were as follows: untreated control, control with vehicle, extract dose A, extract dose B, IL1beta, IL1beta+dose A, IL1beta+dose B, each repeated 3 times.

Endothelial Permeability (Per Screening)

The endothelial cells, held in plates with complete medium (10% serum), were separated, with trypsin/EDTA, and plated in transwell plates, in PET with pores having a diameter of 0.4 micron accommodated in a 12-well multi-plate, at a density of $8 \times 10^4$ cells/transwell. The cells were left to grow for 72 h so as to form a complete monolayer that could be assessed under inverted microscope. Once confluence had been reached, the medium was removed and the extracts were added for 18 h. Without changing the cell medium, IL1beta (10 ng/ml, 1 h) was added where indicated by the protocol. Once the stimulation time had elapsed the medium was removed and 500 µl of FITCH-dextran (3 kDa, 10 µM diluted in PBS) were added in the transwell, whilst 1.5 ml of PBS were introduced into the well of the multi-plate below. Every 15 minutes, 100 µl×3 (triplicate) were sampled from the well of the multi-plate and a fluorescence spectrophotometry reading was taken (485 nm excitation, 535 nm emission). This makes it possible to measure the FITC-dextran that has passed through the barrier formed by the endothelial cells. The results are expressed as a relative value of measured fluorescence.

The test as described above was carried out for each plant forming the mixture of the invention, using extracts of each plant and co-extract of *Solidago virgaurea* and *Orthosiphon stamineus* in the ratio 3:1.

The test was also carried out with the mixture of extracts according to the invention.

The data obtained, shown in FIGS. 2 to 9, shows how the permeability of the lymphatic vessels exposed to cytokine remains greater than that of healthy endothelium (therefore negative effect) with all the single extracts apart from *Orthosiphon stamineus* (FIG. 3) at the lowest tested concentration, which at a higher concentration, however, reduces the level of permeability below the basal value, and *Fagopyrum esculentum* (FIG. 9A), which returns the permeability to values close to basal levels only at the highest tested concentration, demonstrating a weaker protective effect compared with the mixture of the invention. The permeability of the lymphatic vessels is instead held at levels equal to those of healthy endothelium by the mixture of the invention. The data shows, in addition, that the mixture of the invention does not have any undesirable effects on the endothelium not exposed to the tested inflammatory agents.

In particular, FIGS. 8 and 9E, provided with a mixture that comprises co-extract *Solidago virgaurea* and *Orthosiphon stamineus*, show how the selection of the components of the mixture of the invention makes it possible to obtain an optimal synergic effect on holding the vascular permeability at levels similar to that of healthy lymphatic endothelium.

5. Diuretic Activity Test

The animals were housed in metabolic cages (three mice/cage) and were allowed free access to food and drinking water (commercial oligomineral water). In order to obtain similar physiological states of hydration, gavage of oligomineral water of 2.5% body weight was administered to all groups of animals 2 hours before the experiment.
The animals were then divided randomly into groups (9 mice/group) in accordance with the following treatment schema:
1. Untr: untreated group
2. $H_2O$: 100 microl/mouse of oligomineral $H_2O$ were administered by means of gastric probe at t=0 (negative control)
3. Furosemide: 100 microl/mouse of furosemide were administered at 10 mg/kg in oligomineral water by means of gastric probe at t=0 (positive control)
4—Goldenrod: 100 microl/mouse of goldenrod extract (200 mg/kg body weight in oligomineral water) were administered by means of gastric probe at t=0
5—Orthosiphon: 100 microl/mouse of extract of orthosiphon (200 mg/kg body weight in oligomineral water) were administered a t=0
6—Goldenrod: orthosiphon (3:1): 100 microl/mouse of co-extract goldenrod+orthosiphon (200 mg/kg body weight in oligomineral water) were administered by gastric probe at t=0

In order to assess the diuretic activity of the compounds, samples of urine were collected in graduated cylinders, and the volume thereof was recorded at intervals of 2 h up to a total of 8 hours.
The urinary excretion, independently of the weight of the animals, was calculated as total diuresis divided by the volume of total liquid administered.
Urinary excretion=volume of total urine (ml/100 g BW)/total liquid consumed.
The data obtained shows a urinary excretion after 8 hours equal to 2 ml with 200 mg/kg of goldenrod, 2.25 ml with 200 mg/kg of orthosiphon and 3 ml with 200 mg/kg goldenrod+orthosiphon co-extracted in the ratio 3:1.
The urinary excretion in untreated mice was approximately 1.9 ml, in the mice treated with only oligomineral water it was approximately 2.25 ml, and in the mice treated with 10 mg/kg of furosemide it was approximately 3.9 ml.

6. ROS Analysis

The ROS analysis was carried out by placing the HDLEC cells $1.5\times10^3$ in 96-well plates, said cells, after adhesion, being pre-treated with 10 μg/ml of the mixture of the invention for 18 hours and then with IL-1β (10 ng/ml for 1 hour) in medium without phenol red. DCFH2-DA (2.7-dichlorodihydrofluorescein diacetate Invitrogen, Milan, Italy) was added in an amount of 10 μM for 30 minutes, and the intracellular levels of ROS were photometrically assessed using a microplate reader (excitation/emission 495/527, SpectraFluor, Tecan). The results were recorded as RFU (relative fluorescence unit) corrected for the number of cells contacted.

7. Immunofluorescence Analysis

The proteins of occluding tight junction and zona occludens 1 (ZO-1) expressed on the cell surface were visualised using confocal analysis. The cells were plated $5\times10^4$ on 1 cm circular glass slides. After 24 hours the cells were washed and treated with the mentioned stimulants. The immunofluorescence analysis was carried out as reported in the materials and methods of Monti et al, Pharmacol Res 2013; 76:171-81.

8. Western Blot

Cells ($3\times10^5$/plate 6 cm), 90% confluence, were treated or not with the mixture of the invention (10 μg/ml, 18 hours). The expression of the markers of the inflammatory pathways (iNOS, eNOS, COX-2) and of the anti-oxidant/pro-oxidant enzymatic systems (SOD-1, catalase, p22 phox) was assessed by means of western blot as described in the materials and methods of Terzuoli et al. 2014. PLoS One 9: e84358, Monti et al., 2014 J Pharmacol Exp Ther.; 351(3): 500-9. The data was recorded as arbitrary densitometry unit (A.D.U.) of the target protein compared with the beta-actin used as control.

Materials and Reagents

The reagents for cell culture, i.e. rutin and L-NMMA, were Sigma Aldrich (St. Louis, Mo., USA). The foetal bovine serum was Hyclone (Euroclone, Milan, Italy). 3 kDa FITC-dextran was Life Technologies (Carlsbad, Calif., USA). The anti-ZO-1 and anti-eNOS were BD Transduction Laboratories, Milan, Italy. The anti-occludin was Zymed-Life Technologies (Carlsbad, Calif., USA). The anti-iNOS and anti-p22 phox were Santa Cruz Biotechnology, Inc. (Dallas, Tex., USA). The anti-COX-2 was Cayman Chemical Company (Ann Arbor, Mich., USA). The aAnti-SOD-1 was Millipore (Temecula, Calif., USA). The anti-catalase and anti-beta actin were Sigma-Aldrich (St. Louis, Mo., USA).

Analysis of the Data and Statistical Procedures

The results were representative of, or averaged over at least three independent experiments performed in triplicate for each sample. The statistical analysis was carried out using the ANOVA test followed by the Bonferroni and student t tests when appropriate (GraphPad). $P<0.05$ was considered to be statistically significant.

The invention claimed is:
1. A method for treating pathologies associated with lymphatic hyperpermeability in a subject in need thereof, comprising administering an effective amount of a mixture of roots of *Taraxacum officinalis*, leaves of *Fagopyrum esculentum*, rootstock and/or roots of *Ruscus aculeatus*, tops of *Solidago virganrea*, and leaves of *Orthosiphon stamineus* or extracts of said plant parts for treating said pathologies associated with lymphatic hyperpermeability.

2. The method according to claim 1, wherein said pathologies present a deregulation of the integrity of the lymphatic endothelium.

3. The method according to claim 2, wherein said pathologies are selected from the group consisting of chronic inflammation, lymphedema, lipedema, circulatory stasis, and water retention pathology.

* * * * *